United States Patent [19]
Sanders

[11] Patent Number: 5,935,909
[45] Date of Patent: *Aug. 10, 1999

[54] TREATMENT OF TREE SEEDLINGS TO ENHANCE SURVIVAL RATE

[75] Inventor: J. Larry Sanders, Lockport, Ill.

[73] Assignee: Donlar Corporation, Bedford Park, Ill.

[*] Notice: This patent is subject to a terminal disclaimer.

[21] Appl. No.: 08/931,428

[22] Filed: Sep. 16, 1997

[51] Int. Cl.⁶ .............................. A01N 59/06; A01N 3/02; A01N 37/44
[52] U.S. Cl. ......................... 504/320; 504/115; 504/147
[58] Field of Search .................................... 504/320, 147, 504/115

[56] References Cited

U.S. PATENT DOCUMENTS

| | | | |
|---|---|---|---|
| 4,172,072 | 10/1979 | Ashmead | 260/115 |
| 4,799,953 | 1/1989 | Danzig et al. | 71/98 |
| 4,813,997 | 3/1989 | Kinnersley et al. | 71/66 |
| 4,839,461 | 6/1989 | Boehmke | 528/363 |
| 4,863,506 | 9/1989 | Young | 71/113 |
| 4,863,898 | 9/1989 | Ashmead et al. | 514/6 |
| 5,059,241 | 10/1991 | Young | 71/106 |
| 5,350,735 | 9/1994 | Kinnersley et al. | 504/147 |
| 5,580,840 | 12/1996 | Harms et al. | 504/115 |
| 5,593,947 | 1/1997 | Kinnersley et al. | 504/283 |
| 5,635,447 | 6/1997 | Sanders | 504/134 |
| 5,646,133 | 7/1997 | Sanders | 514/86 |
| 5,661,103 | 8/1997 | Harms et al. | 504/147 |

OTHER PUBLICATIONS

Agri Finance, Apr. 1993, *Technological breakthrough on fertilizer use*, pp. 16–17.
Kinnersley et al., Plant Growth Regulation 9:137–146 (1990).
Byrnes, Fertilizer Research 26:209–215 (1990).
Farm Chemicals Handbook, 1987, Meister Pub. Co., Willoughby, Ohio, p.B10.

*Primary Examiner*—S. Mark Clardy
*Assistant Examiner*—Marina Lamm
*Attorney, Agent, or Firm*—Zarley, McKee, Thomte, Voorhees & Sease

[57] ABSTRACT

Tree seedlings, especially pine tree nursery seedlings, are treated, for example, by a root soak with a water-soluble, polyorganic acid, having a molecular weight size of more than 1,500 Daltons. Particularly suitable for this purpose are polyamino acids such as polyaspartic acid.

11 Claims, No Drawings

TREATMENT OF TREE SEEDLINGS TO ENHANCE SURVIVAL RATE

FIELD OF THE INVENTION

The field of the invention is reforestation with tree seedlings, particularly pine seedlings. Survivability and re-growth rate for reforestation tree seedlings is a particular problem.

BACKGROUND OF THE INVENTION

This invention relates to enhancing the survival rate and the re-growth rate of tree seedlings. Both survival rate and re-growth rate are problems in tree seedling transplanting as used for reforestation.

Survival rate, as used herein, refers to the number of transplanted tree seedlings that survive. In a typical reforestation process, depending upon the climatic conditions at the time of reforestation, survival rates of the transplanted tree seedlings can be as low as one out of three. In a typical wet year, the survival rate might be as high as 70% to 80%, or even up to 100%. When the survival rate is lower, it is often necessary to replant the stand. This, of course, increases the cost per acre dramatically. In fact, when labor costs are considered the cost per acre for replanting is nearly as much as the cost per acre in the original reforestation.

Re-growth rate refers to the rate of growth of the transplanted seedling. It is generally measured as growth at the top of the plant. Transplanted tree seedlings, when they are moved from the nursery to the field, always run the risk of transplant shock. It is inevitable that a certain percentage of the plants in fact will undergo transplant shock. This is costly to the reforestation process, since in transplant shock the plant, while it may survive, in fact will be dwarfed in size by surrounding trees, meaning that it will be forever deprived as it competes. Transplant shock can in fact essentially "stall growth" for up to as much as a year. Accordingly, there is a need to minimize transplant shock and enhance the rate of re-growth so that all of the transplanted seedlings start on an equal footing as they compete for nutrients and energy.

It can be seen that there is a real and continuing need for an effective method of enhancing survival rate and re-growth rate of tree seedlings transplanted from the nursery to the field. This invention has as its primary objective the fulfillment of this need.

In another objective of the present invention, survival rate and re-growth rate for tree seedlings are enhanced by an environmentally friendly, non-objectionable treatment.

A yet further objective of the present invention is to provide an economical, non-toxic, biodegradable and environmentally friendly treating composition which does not pollute the surrounding soil, and which is relatively inexpensive, and which can effectively function with nutrient added ingredients if desired.

The method and manner of accomplishing each of the above objectives will become apparent from the detailed description of the invention.

SUMMARY OF THE INVENTION

A method of enhancing the survival rate and the growth rate of tree seedlings, especially pine tree seedlings, during reforestation. The tree seedling is treated with a small but survival and growth enhancing effective amount of water-soluble polyamino organic acid, preferably a polyaspartic acid. The treatment dramatically increases survival rate of the tree seedlings and minimizes the number of seedlings that undergo transplant shock.

DETAILED DESCRIPTION OF THE INVENTION

In accordance with the present invention, tree seedlings are treated with a water-soluble, polymeric amino acid. Surprisingly, it has been found that when this is done the rate of survival of the tree seedlings and the re-growth rate of the tree seedlings are dramatically increased. The preferred polyamino acid is polyaspartic acid.

In general, the polymeric organic amino acids can be made available to the plant in root soak solutions containing at least about 0.1 parts per million (ppm) by weight, preferably about 1000 to about 400,000 parts per million (ppm) by weight, more preferably about 10,000 to about 100,000 ppm by weight, of the polymeric organic acid in the solution. Such solutions can have other nutrients added, if desired. Solutions containing the polymeric organic acid can be applied in a root soak or in the plant hole by spraying on the roots, etc., as discussed below. The preferred method, however, is root soak. Solutions containing the polymeric organic amino acid are also useful in conjunction with certain other plant nutrients.

The time of the soak can be from a time sufficient for a root dip to from 0.5 hours to 4.0 hours, with a preferred root soak time occurring from about 0.25 hours to 2.5 hours.

The process herein is particularly suitable for reforestation of pines. However, the tree seedlings can be either hardwoods or softwoods. Examples of suitable softwoods, of course, include pine, birch and poplar. Examples of suitable hardwoods would include oak, walnut, maple, cherry and the like. It can also be used with rubber, coffee, tea, cocoa, Pacific yew, oil palm and citrus trees.

While much of the description herein is given in conjunction with a root soak of the tree seedling in the nursery, it should be understood that other ways and times of treatment can occur. For example, the treatment can occur at the planting site by directly placing the polyamino acid such as polyaspartic acid in the soil opening along with the tree seedling, either in loose form or in a packet, similar to a tea bag. If packets are used, they of course need to be non-toxic, water permeable and biodegradable.

Polymeric organic acids having a molecular weight in excess of about 100,000 usually do not exhibit adequate solubility in water for the present purposes, thus for present purposes a polymeric organic acid molecular size not larger than about 100,000 is preferred. Particularly preferred molecular weight is in the range of about 2,000 to about 30,000.

The polymeric organic acids of the present invention may be polymeric amino acids, which can be applied to soil in a water solution or as a solid in the anhydro form as, for example, anhydropolyaspartic acid (polysuccinimide). Polysuccinimide or polysuccinimide copolymers can be mixed with sodium carbonate or sodium bicarbonate and applied as a powder, as a dry granule or in pellet form. The sodium carbonate and sodium bicarbonate will hydrolyze polysuccinimide to polyaspartic acid sodium salt in moist soil. Polysuccinimide can also be applied to soil as a powder, pellet or as granules mixed with limestone (Ca and Mg carbonate). In this application the carbonates of the limestone can hydrolyze the polysuccinimide or polysuccinimide copolymer to a water soluble salt in moist or wet soil. Another way of using polysuccinimides is to apply it to soil as a powder, granule or pellet after the soil has received an injection of ammonia. In this process ammonium hydroxide formed from the ammonia and water in the soil will hydrolyze the succinimide moieties in the polymer to water soluble aspartic acid moieties.

The polymeric organic acids, to be suitable for the practice of the present invention, must be or become water soluble, and must have a molecular size sufficiently large to preclude absorption into the plant's own system, generally between 1500 and 100,000 daltons. To that end, the organic acids deemed suitable for the present purposes, while hydrophilic, have a weight average molecular weight (Mw) larger than 1,500 daltons and have at least about 15 repeating organic acid units (residues), or mers, in the linear polymer chain that constitutes the polymeric acid. Such linear polymer chains can be cross-linked if desired, but only to a degree that does not materially affect the water solubility of the polymeric moiety. Particularly preferred molecular size is in the range of Mw about 2,000 to about 50,000.

Illustrative are polymeric acids, with or without carboxylic acid, thiocarboxylic acid, mercapto, hydroxy, imidocarboxy, and/or amino side chains, such as, for example, polyglutamic acid, polysuccinimide, polyaspartic acid, polyglycine, polycysteine, polycysteine/glutamic acid, polyserine, polycysteine/glutamic/aspartic acid, mixtures of the foregoing, and the like. Block or random copolymers or terpolymers of several amino acids and other co-monomers are also within the purview of the present invention as the polymeric organic acid component thereof. For example, the utilized polymeric organic acid component can be a block or random copolymer containing (a) at least one amino acid derived moiety selected from the list including aspartic acid and glutamic acid, and optionally (b) one or more co-monomers selected from the list including mono, di or multifunctional monomer containing amino, hydroxyl and carboxyl functional groups such as polybasic carboxylic acids and anhydrides, fatty acids, polybasic hydroxycarboxylic acids, monobasic polyhydroxycarboxylic acids, alcohols, amines, di and triamines, polyamines, alkoxylated alcohols and alkoxylated amines, alkoxylated diamines and triamines, amino sugars, carbohydrates, sugar carboxylic acids, amino acids, non-protein forming aminocarboxylic acids, lactams, lactones, diols, triols, polyols, unsaturated dicarboxylic and tricarboxylic acids, unsaturated monocarboxylic acids, derivatized aspartic acid residues, and derivatized glutamic acid residues, and (c) wherein the sum of the aspartic and/or glutamic acid residues is at least about 20% of the total number of residues in the polymer.

The polymeric organic acids of the present invention can also be water soluble polymers selected from the group consisting of polylactic acid, polyglycolic acid, polyepoxysuccinic acid, polyacrylic acid, polymaleic acid, polyacrylamide, acrylamide-acrylic acid copolymers poly (vinyl alcohols), acrylamide/2-acrylamido-2-methylpropanesulfonic acid copolymers, acrylamide/ diallyldimethylammonium chloride copolymers, acrylamide/dimethylaminoethyl methacrylate and acrylate copolymers and methyl chloride or sulfate quaternized derivatives of these copolymers, polyvinylpyrrolidone, acrylic acid/maleic acid copolymers, polyitaconic acid, acrylic acid/itaconic acid copolymers, maleic acid/itaconic acid copolymers, polymethacrylic acid, methacrylic acid/ acrylamide copolymers and methacrylic acid/acrylic acid copolymers and natural or synthetic polyphenols.

Polymeric organic acids for use in the present invention can be made, inter alia, by any of several methods known in the chemical art. For example, polymeric organic acids containing mono, di or multifunctional monomers that have amino, hydroxyl and carboxyl functional groups such as polybasic carboxylic acids and anhydrides, fatty acids, polybasic hydroxycarboxylic acids, monobasic polyhydroxycarboxylic acids, alcohols, amines, di and triamines, polyamines, alkoxylated alcohols and alkoxylated amines, alkoxylated diamines and triamines, amino sugars, carbohydrates, sugar carboxylic acids, amino acids, nonprotein forming aminocarboxylic acids, lactams, lactones, diols, triols, polyols, unsaturated dicarboxylic and tricarboxylic acids, unsaturated monocarboxylic acids can be made by a variety of methods described in the literature.

For example, U.S. Pat. No. 5,510,427 to Wood, incorporated herein by reference, describes a method of preparing polyaspartate copolymers by polymerization of maleic acid, and ammonia with a diamine or triamine, followed by hydrolysis with base. U.S. Pat. No. 5,494,995 to Wood, incorporated herein by reference, describes a method of preparing polysuccinimide copolymers by polymerization of maleic acid, ammonia and a polycarboxylic acid, and optionally with a diamine or triamine. U.S. Pat. No. 5,484, 860 to Wood, incorporated herein by reference, describes a method of preparing polyaspartate copolymers by polymerization of maleic acid, ammonia and a polycarboxylic acid, and optionally with a diamine or triamine, followed by hydrolysis with base; U.S. Pat. No. 5,478,919, to Koskan, incorporated herein by reference, describes a method of preparation of copolymers of polysuccinimide or polyaspartic acid by co-polymerization of maleic or fumaric acid, ammonia and one or more amino, hydroxyl or carboxyl containing monomer. U.S. Pat. NO. 4,696,981, to Harada, incorporated herein by reference, describes the co-polymerization of maleic or fumaric acid, ammonia and one or more amino acids using microwave heating, to form polysuccinimide copolymers. U.S. Pat. No. 4,892,733, to Bichon, incorporated herein by reference, describes copolymers of aspartic or glutamic acid with other natural amino acids. German laid open document No. 4221875, incorporated herein by reference, describes a method of preparing copolymers of polysuccinimide and polyaspartic acid by co-polymerization of aspartic acid with 99 to 0.1 mole % of one or more polybasic carboxylic acids, polybasic carboxylic acid anhydrides, fatty acids, polybasic hydroxycarboxylic acids, monobasic polyhydroxycarboxylic acids, alcohols, amines, di and triamines, polyamines, alkoxylated alcohols and alkoxylated amines, alkoxylated diamines and triamines, amino sugars, carbohydrates, sugar carboxylic acids, amino acids, non-protein forming aminocarboxylic acids, or by radically initiated graft polymerization of monoethylenically unsaturated carboxylic acids in the presence of polyaspartic acid.

Examples of co-monomers useful in the polymers of the present invention include, but are not limited to, lactic acid, citric acid, glycolic acid, malic acid, tartaric acid, succinic acid, adipic acid, butane-tetracarboxylic acid, gluconic acid, glucuronic acid, glucaric acid, aconitic acid, sulfosuccinic acid, phosphinicosuccinic acid, phosphonosuccinic acid, iminodiacetic acid, nitrilotriacetic acid, stearic acid, palmitic acid, cyclohexanedicarboxylic acid and anhydride, terephthalic acid, phthalic acid and anhydride, crotonic acid, sorbitol, glycerol, glucose, fructose, sucrose, maltose, glycine, alanine, serine, theonine, cystine, cysteine, ethylenediamine, diethylenetriamine, triethylenetetramine, polyamines, 1,6-diaminohexane, octadecylamime, glucosamine, alkoxylated amines, alkoxylated diamines and triamines, 6-amiriocaproic acid, 4-aminobutyric acid, diaminocyclohexane, urea, melamine, carbohydrazide, hydrazine, ascorbic and isoascorbic acid, sorbic acid, maleuric acid, cyanuric acid, alkyldiamines, alkyltriamines, acrylic acid, methacrylic acid, maleic acid and anhydride, alkylmaleic acids, alkenylsuccinic acids and anhydrides, methylenemalonic acid.

Examples of derivatized aspartic acid and derivatized glutamic acid residues include materials in which the free carboxyl group of the aspartic acid or glutamic acid residue has been chemically bonded with an amino, hydroxyl or mercapto containing moiety to form an amide, ester or thioester bond.

Non-limiting examples of polymeric organic acids containing derivatized aspartic acid or glutamic acid residues, useful in the methods of the present invention, are found in the following references: U.S. Pat. No. 5,506,335 to Uhr, incorporated herein by reference, discloses polyaspartate alkyl and aryl amide derivatives with sulfonic acid group-containing side chains on the alkyl or aryl moieties. U.S. Pat. No. 4,363,797 to Jacquet, incorporated herein by reference, describes derivatized polyaspartates bearing amide, mercapto and sulfoalkylamide functional group bearing moieties attached to the polyaspartate by amide bonds to the free carboxyl groups of the polymer. U.S. Pat. No. 4,314,808 to Jacquet, incorporated herein by reference, describes derivatized polyaspartates wherein alkyl substituents, functionalized alkyl substituents, dyes and dye precursors are attached to the polyaspartate by amide bonds to the free carboxyl groups of the polymer. U.S. Pat. No. 3,846,380 to Fujimoto, incorporated herein by reference, describes derivatized polyaspartates wherein C1 to C20 alkyl groups, in proportions from 0.005 to 1 substituents per monomer unit, are attached to the polyaspartate by amide bonds to the free carboxyl groups of the polymer. European Patent disclosure number EP 685504 to Katoh, incorporated herein by reference, describes polyaspartates with pendant amino acid and amino acid ester groups attached to the polyaspartate by amide bonds to the free carboxyl groups of the polymer. European Patent disclosure number EP 439846, incorporated herein by reference, discloses derivatized polyaspartates and polyglutamates with pendant 2-hydroxyethylamide groups, wherein some or all of the hydroxyl groups have been esterified with carboxylic acids. French Patent Publication FR 2424292, to Jacquet, incorporated herein by reference, discloses amide derivatives of polyaspartic acid formed by reaction of polysuccinimide with at least one primary amine, secondary amine, or hydroxyalkyl amine; also disclosed are amide derivatives of polyaspartic acid with quaternary amine substituents such as $NH(CH_2)_3N(CH_3)_3^+Z^-$ wherein $Z^-$ is a halide ion or methylsulfonate ion. PCT Application number WO 94/20563, to Kroner, incorporated herein by reference, discloses a method of derivatizing polysuccinimide with amino acids by reaction of polysuccinimide with amino acids in aqueous medium at pH values wherein at least 5% of the amino acids are in the free amine (nonprotonated) form. PCT Application number WO 96/04332, to Greindl, incorporated herein by reference, discloses derivatives of polyaspartic acid having hydroxamic acid, hydroxamic ether and/or hydrizide groups in the side chain, formed by reaction of polysuccinimide with hydroxylamine, hydroxylamine alkyl ethers with 1 to 18 C atoms in the alkyl group, N-mono-alkyl hydroxylamines with 1 to 18 C atoms in the alkyl group, and/or hydrazine in aqueous or alcohol media at pH values of at least 7.

Examples of amino, hydroxyl or mercapto containing moieties that may be bonded with aspartic acid or glutamic acid residues to form derivatized aspartic acid or derivatized glutamic acid residues include, but are not limited to: hydrazine, C1–C20 alkyl or aryl substituted hydrazines, hydroxyl amine, C1–C20 alkyl O-substituted hydroxylamines, natural amino acids such as alanine, glycine, leucine, phenylalanine, lysine, non-natural amino acids such as 6-aminocaproic acid, 4-aminobuteric acid, 2-aminobenzoic acid, 4-aminobenzoic acid, or iminodiacetic acid, C1–C20 alkyl amines, aryl amines such as aniline, secondary alkyl amines such as dimethylamine, morpholine, diethylamine, or N-methylsterylamine, substituted alkyl or aryl amines such as taurine, 3-phosphinopropyl amine, or 4-aminobenzenesulfonic acid, C1–C20 alcohols, amino alcohols such as ethanolamine, diethanolamine, or triethanolamine, heterocyclic amines such as 2-aminopyridine, 2-aminopyrazine, 2-aminothiazole, or 2-aminoimidazole, diamines such as ethylenediamine, hexamethylenediamine, or alkoxylated diamines such as triethyleneglycol diamine, alkoxylated amines such as amine capped polyethylene oxides or amine capped polypropylene oxides, polyols such as ethylene glycol, propylene glycol, glycerin, polyethylene oxides, polypropylene oxides, sugars, or amino sugars, thiols such as butanethiol, 2-hydroxyethanethiol, or 2-aminoethanethiol, and hydroxycarboxylic acids such as glycolic acid, lactic acid, 2-hydroxybuteric acid, citric acid, tartaric acid, or salicylic acid.

The preferred polymeric organic acids of the present invention are those polymers in which the sum of the aspartic acid and glutamic acid residues is greater than about 20% of the total number of polymeric residues. More preferred are polymers wherein the sum of the aspartic acid and glutamic acid residues is greater than about 30% of the total number of polymeric residues. Most preferred are polymers wherein the sum of the aspartic acid and glutamic acid residues is greater than about 50% of the total number of polymeric residues.

The starting materials for the polymerization to form polymeric organic acids of the present invention, i.e., the amino acids and other co-monomers, can exist as optical isomers, depending upon their respective structures, and can be polymerized either as a racemic mixture or as segregated optical isomers.

The aspartic acid moieties of the polymeric organic acids of the present invention may be derived from the thermal polymerization of aspartic acid or of precursors of aspartic acid such as maleamic acid, fumaramic acid, ammonium salts of maleic acid, ammonium salts of fumaric acid and ammonium salts of malic acid.

Particularly well suited for the practice of the present invention are the non-chelating polyorganic acids such as polyacrylic acid and the like, as well as the polyamino acids such as polyaspartic acid having a molecular weight in the range of about 3,000 to about 28,000, polyglutamic acid having a molecular size in the range of about 4,000 to about 14,000, polyglycine having a molecular weight in the range of more than 1,500 to about 7,000, and copolymers of aspartic acid with other carboxylates or amine containing monomers.

The amount of polyaspartic acid in the treating composition can vary widely, but satisfactory results are obtained when it is from about 1000 parts per million to about 400,000 parts per million, preferably from about 10,000 per million to about 100,000 parts per million. It may be used alone or in combination with known nutrients or additives such as citric, phosphoric or acetic acid or suitable salts thereof and biocides. If desired, agents may also be added to enhance wetting or capillary action up the plant stem.

The following examples are offered to further illustrate, but not limit the process of this invention.

In the examples below, the study described demonstrates the effect of polyaspartic acid on the survival rate of pine seedling transplants under normal reforestation conditions. Pine tree seedlings had their roots soaked in water at three varying levels of polyaspartic acid solution for a period of 2 hours. The seedlings were then transplanted in a normal fashion and allowed to grow under normal conditions. Transplanting occurred on March 1st, and on June 15th observations and measurements were taken regarding tree survival and the amount of re-growth that had taken place. The rates of polyaspartic acid used in the study were 25,000 ppm, 50,000 ppm and 100,000 ppm. 17 seedlings were treated in each group, and individual seedlings were counted for survival and measured for re-growth compared to the original height. The polyaspartic acid used was a 40% solution of a polymer having a molecular weight of 5,000. A control of water only as a root soak was also used. Table 1 shows a summary of the data on pine seedling survival and re-growth. Table 2 shows the effect of water and the polyaspartic acid solution used as a pre-transplant presoak for reforestation pine seedlings with the seedlings all soaked for 2 hours prior to transplanting. Table 2 shows the details for each seedling.

TABLE 1

Effect of Polyaspartic Nutrient Absorption
Enhancer on Pine Seedling Survival and Re-Growth

| | Seedling survival (of 17 originals) | Seedling Growth inches |
|---|---|---|
| Control, water | 4 | 0.00 |
| 25,000 ppm | 5 | 1.50 |
| 50,000 ppm | 14 | 5.39 |
| 100,000 ppm | 12 | 2.75 |
| $LSD_{.05}$ | 0.3 | 1.22 |

Water-polyaspartic solution used as a pre-transplant presoak for reforestation pine seedlings. All plants soaked for 2 hours prior to transplanting.

TABLE 2

Effect of water and polyaspartic solution used as a pre-transplant presoak for reforestation pine seedlings. All plants soaked for 2 hours prior to transplanting.

TREATMENT

| | Water | | 25,000 ppm AmiSorb | | 50,000 ppm AmiSorb | | 100,000 ppm AmiSorb | |
|---|---|---|---|---|---|---|---|---|
| Replication | Survival | Re-growth (inches) | Survival | Re-growth (inches) | Survival | Re-growth (inches) | Survival | Re-growth (inches) |
| 1 | 1 | 0.00 | 1 | 4.00 | 1 | 5.50 | 1 | 2.50 |
| 2 | 1 | 0.00 | 1 | 0.00 | 1 | 6.50 | 1 | 6.50 |
| 3 | 1 | 0.00 | 1 | 0.50 | 1 | 4.50 | 1 | 2.50 |
| 4 | 1 | 0.00 | 1 | 1.50 | 1 | 5.50 | 1 | 1.00 |
| 5 | 0 | 0.00 | 1 | 1.50 | 1 | 9.00 | 1 | 0.50 |
| 6 | 0 | 0.00 | 0 | 0.00 | 1 | 7.00 | 1 | 4.00 |
| 7 | 0 | 0.00 | 0 | 0.00 | 1 | 6.00 | 1 | 0.50 |
| 8 | 0 | 0.00 | 0 | 0.00 | 1 | 4.00 | 1 | 2.00 |
| 9 | 0 | 0.00 | 0 | 0.00 | 1 | 4.50 | 1 | 3.50 |
| 10 | 0 | 0.00 | 0 | 0.00 | 1 | 3.50 | 1 | 4.50 |
| 11 | 0 | 0.00 | 0 | 0.00 | 1 | 3.00 | 1 | 2.50 |
| 12 | 0 | 0.00 | 0 | 0.00 | 1 | 1.50 | 1 | 3.00 |
| 13 | 0 | 0.00 | 0 | 0.00 | 1 | 8.00 | 0 | 0.00 |
| 14 | 0 | 0.00 | 0 | 0.00 | 1 | 7.00 | 0 | 0.00 |
| 15 | 0 | 0.00 | 0 | 0.00 | 0 | 0.00 | 0 | 0.00 |
| 16 | 0 | 0.00 | 0 | 0.00 | 0 | 0.00 | 0 | 0.00 |
| 17 | 0 | 0.00 | 0 | 0.00 | 0 | 0.00 | 0 | 0.00 |
| Count/Mean | 4 | 0.00 | 5 | 1.50 | 14 | 5.39 | 12 | 2.75 |

As can be seen from the above, the amount of re-growth and the survival was best with the 50,000 ppm solution. Moreover, the re-growth was dramatic in comparison with the control, and the survival rate was 14 seedlings compared to 4 in the water control. The effect of the seedling treatment is therefore readily established.

What is claimed is:

1. A method of enhancing survival rate and re-growth rate of tree seedlings, comprising:
    root soaking tree seedlings with a water-soluble,
    non-aromatic polyorganic acid which is a polyamino acid of the group consisting of polyaspartic acid, polyglutamic acid, and copolymers of aspartic acid and glutamic acid with other carboxylates or amine containing monomers, said polyamino acid having at least a molecular weight larger than 1,500;
    wherein the polyamino acid is present in an aqueous solution in a concentration of from about 10,000 to 100,000 ppm;
    and further providing that the root soaking occurs for a time period of 0.5 to 4.0 hours.

2. The method of claim 1 wherein the polyamino acid is polyaspartic acid.

3. The method of claim 1 wherein the root soaking occurs for from 1.0 hours to 2.5 hours.

4. The method of claim 3 wherein the tree seedling is one selected from the group consisting of hardwoods and softwoods.

5. The method of claim 4 wherein the tree seedling is a softwood.

6. The method of claim 5 wherein the tree seedling is pine.

7. A method of enhancing survival rate and re-growth rate of tree seedlings, comprising:
    placing in a tree seedling plant hole a tree seedling and a water soluble, non-aromatic polyorganic acid which is a polyamino acid of the group consisting of polyaspartic acid, polyglutamic acid, and copolymers of aspartic acid and glutamic acid with other carboxylate or amine containing monomers, said polyamino acid having at least a molecular weight larger than 1500;
    wherein the polyorganic acid is placed in the tree seedling plant hole by spraying the polyorganic acid on the roots of the tree seedling plant.

8. The method of claim 7 wherein the polyamino acid is polyaspartic acid.

9. The method of claim 8 wherein the tree seedling is a pine seedling.

10. A method of enhancing survival rate and re-growth rate of tree seedlings, comprising:
    root soaking tree seedlings with a water-soluble, non-aromatic polyorganic acid which is a polyamino acid of the group consisting of polyaspartic acid, polyglutamic acid, and copolymers of aspartic acid and glutamic acid with other carboxylates or amine containing monomers, said polyamino acid having at least a molecular weight larger than 1,500;

wherein the polyamino acid is present in an aqueous solution in a concentration of 25,000 to 100,000 ppm;

and further providing that the root soaking occurs for a time period of at least 2 hours by placing the polyamino acid in the soil opening along with the tree seedling in loose form or in a packet.

11. A method according to claim 10 wherein the polyamino acid is present in the aqueous solution in a concentration of 50,000 ppm.

* * * * *